United States Patent
Adamson et al.

(10) Patent No.: US 9,981,139 B2
(45) Date of Patent: May 29, 2018

(54) ACOUSTIC TRANSMITTER AND IMPLANTABLE RECEIVER

(71) Applicant: Dalhousie University, Halifax (CA)

(72) Inventors: Robert B. A. Adamson, Halifax (CA); Jeffrey R. Leadbetter, Dartmouth (CA); Jeremy A. Brown, Halifax (CA); Manohar Bance, Halifax (CA)

(73) Assignee: Dalhousie University, Halifax (CA)

( * ) Notice: Subject to any disclaimer, the term of this patent is extended or adjusted under 35 U.S.C. 154(b) by 161 days.

(21) Appl. No.: 14/783,675

(22) PCT Filed: May 8, 2014

(86) PCT No.: PCT/CA2014/050436
§ 371 (c)(1),
(2) Date: Oct. 9, 2015

(87) PCT Pub. No.: WO2014/179886
PCT Pub. Date: Nov. 13, 2014

(65) Prior Publication Data
US 2016/0059012 A1    Mar. 3, 2016

Related U.S. Application Data

(60) Provisional application No. 61/821,185, filed on May 8, 2013.

(51) Int. Cl.
| | | |
|---|---|---|
| *A61N 1/378* | (2006.01) | |
| *H01L 41/053* | (2006.01) | |
| *H01L 41/37* | (2013.01) | |
| *B06B 1/06* | (2006.01) | |
| *A61M 1/12* | (2006.01) | |

(Continued)

(52) U.S. Cl.
CPC .......... *A61N 1/3787* (2013.01); *A61M 1/127* (2013.01); *A61N 1/0541* (2013.01); *B06B 1/0633* (2013.01); *B06B 1/0644* (2013.01); *H01L 41/053* (2013.01); *H01L 41/113* (2013.01); *H01L 41/18* (2013.01); *H01L 41/37* (2013.01); *A61M 1/12* (2013.01); *A61M 5/14276* (2013.01); *A61M 2205/82* (2013.01); *A61M 2205/8237* (2013.01); *A61N 1/36036* (2017.08); *H01L 41/183* (2013.01); *H04R 2225/31* (2013.01); *H04R 2225/67* (2013.01)

(58) Field of Classification Search
CPC ................ A61N 1/3787; A61N 1/0541; A61N 1/36036; B06B 1/0644; B06B 1/0633; H01L 41/113; H01L 41/18; H01L 41/37; H01L 41/053; H04R 2225/31; A61M 2205/82; A61M 2205/8237; A61M 1/127; A61M 1/12
See application file for complete search history.

(56) References Cited

U.S. PATENT DOCUMENTS

5,844,349 A * 12/1998 Oakley ................... B06B 1/064
                                                  310/340
6,014,898 A    1/2000 Finsterwald et al.
(Continued)

*Primary Examiner* — Michael Kahelin
(74) *Attorney, Agent, or Firm* — Ryan W. Dupuis; Ade & Company Inc.; Kyle R. Satterthwaite (57) ABSTRACT

Among other things, in general, an acousto-mechanical transducer for the interconversion of electricity and acoustic waves is described. Methods are also described for the construction of such transducers.

7 Claims, 9 Drawing Sheets

(51) Int. Cl.
  *A61N 1/05*    (2006.01)
  *H01L 41/113*  (2006.01)
  *A61N 1/36*    (2006.01)
  *H01L 41/18*   (2006.01)
  *A61M 5/142*   (2006.01)

(56) References Cited

U.S. PATENT DOCUMENTS

| | | | |
|---|---|---|---|
| 7,141,919 | B1 | 11/2006 | Hamada et al. |
| 7,949,396 | B2 | 5/2011 | Mi et al. |
| 8,082,041 | B1 | 12/2011 | Radzienski |
| 8,279,712 | B2 | 10/2012 | Korbler et al. |
| 2006/0149329 | A1* | 7/2006 | Penner ............... A61B 5/0028 607/32 |
| 2006/0235300 | A1* | 10/2006 | Weng ............... A61B 17/0057 600/439 |
| 2009/0230823 | A1* | 9/2009 | Kushculey ............... A61N 7/02 310/366 |
| 2014/0155747 | A1* | 6/2014 | Bennett ............... B06B 1/0625 600/439 |

* cited by examiner

ACOUSTIC TRANSMITTER AND IMPLANTABLE RECEIVER

CROSS-REFERENCE TO RELATED APPLICATIONS

This application claims priority to U.S. Provisional Patent Application Ser. No. 61/821,185, filed May 8, 2013, which is hereby incorporated by reference in its entirety.

BACKGROUND

An increasing number of active medical implants that require an electrical power source are being developed. Such devices include pacemakers, artificial hearts, drug pumps, neural stimulators, cochlear implants, retinal implants, and various other sensors, monitors and interfacing medical devices. Traditionally such devices have been powered by implanted batteries in the case of low-power devices (e.g., <1 mW), or via a magnetic induction link in the case of higher power devices (e.g., >1 mW). Magnetic induction links include two coils, one external and one implanted. When a current is driven through the external coil, a voltage is induced on the internal coil through magnetic induction that can be used to power the implanted device. Magnetic induction coils suffer from several major disadvantages, however. A main source of inefficiency is in ohmic heating of the transmit coil which can only be alleviated by increasing the diameter of the wire used in the coil which generally increases the size of the device. For example, the induction coils used to power cochlear implants with 30-80 mW typical power consumption are at least 50 mm in diameter. The large size of the external coil unit makes it hard to attach to the body without also implanting a permanent magnet. This improves the grip of the coil unit during charging; however, magnets can interfere with MRI scanning, an increasingly common diagnostic tool. Additionally, for the transmission of very large amounts of power (e.g., >1 W), the heating of the external coil can make the external unit hot, causing discomfort to the patient.

As an alternative to magnetic induction links, acoustic energy can be used to transmit power to the implanted device. This method uses an external send transducer to convert electrical energy into acoustic energy/waves and directs this energy through the patient's skin toward an implanted receive transducer that converts the acoustic energy back to electrical energy. The received electrical energy may be used to directly power a medical device or may be stored in a capacitor or a battery for later use. Several researchers have proposed devices that use acoustic energy to power implanted medical devices. To date, such devices have been limited by their low efficiency, their high sensitivity to alignment, and safety issues surrounding the heating of tissues. In recent years piezoelectric materials with a higher inherent electromechanical coupling coefficient have become available, notably the relaxor-PT materials. Such materials have made possible the achievement of high power transmission efficiencies (>20%) through several millimeters of tissue, but acoustic power transmission has still not supplanted inductive links. There are a number of reasons for this: acoustic links have historically required a high degree of angular and lateral alignment between the send and receive transducer; the receive transducer must be packaged in a hermetic, yet still acoustically transparent manner, which is difficult to achieve; and impedance matching to a load is often inefficient. Thus, there remains a need to produce more efficient, reliable, and easy-to-use acoustic-link power conversion systems for active implantable medical devices.

SUMMARY

A power conversion system that interconverts electrical and acoustic energy with a high transmission efficiency is disclosed herein. The system can be fabricated so as to produce hermetic and acoustically transparent packaging for implantable receive transducers. The system can also be fabricated so as to minimize issues of angular and lateral alignment. Methods for manufacture of send/receive transducers and power conversation systems are also disclosed.

In general, in an aspect, an acousto-mechanical transducer for use with an active implantable device is described, which is capable of conversion of electricity into acoustic waves or vice-versa, having a piezoelectric material with a front and a back and a backing spacer that contacts the piezoelectric material at its periphery. Implementations may include one or more of the following features. The material has pillars that are electrodes such the each of the pillars is in an electrically isolated region. The pillars are surrounded by filler material. The material is electroded such that each of the pillars is in an electrically isolated region.

In general, in an aspect, an acousto-mechanical transducer for use with an active implantable device is described, which is capable of conversion of electricity into acoustic waves or vice-versa, having a piezoelectric material with a front and a back and pillars of piezoelectric material that are surrounded with filler material. Implementations may include one or more of the following features. The pillars are electroded such that each of the pillars is in an electrically isolated region. There is a backing spacer that contacts the piezoelectric material at its periphery.

In general, in an aspect, an acousto-mechanical transducer for use with an active implantable device is described, which is capable of conversion of electricity into acoustic waves or vice-versa, having a piezoelectric material with a front and a back and pillars of piezoelectric material that are electroded such that each of the pillars is in an electrically isolated region. Implementations may include one or more of the following features. The pillars are surrounded by a filler material. There is a backing spacer that contacts the piezoelectric material at its periphery.

Implementations of any of the above may include one or more of the following features. The piezoelectric material (and that of the pillars if present) comprises single-crystal relaxor-PT ferroelectric material. The piezoelectric material comprises PMN-PT. The piezoelectric material is curved. The piezoelectric material is shaped as a spherical cap. The filler material (if present) contains epoxy. The backing spacer (if present) is toroidal. The backing spacer further includes an acoustic spacer topped with pins that have an equal length, such that each of the acoustic spacer's pins reaches beyond the front of the piezoelectric material. There is a structural support that adheres to the backing spacer opposite the back of the piezoelectric material, producing an air pocket between the two. The structural support has a via. The via is filled. There is an electrical connection that runs from the piezoelectrial material through the air pocket and a filled via to a point outside the transducer. The acoustic spacer is circular. The structural support overhangs to attach to a side casing, which is in turn adhered to the structural support at its periphery. The side casing includes titanium. The side casing is circular. There is a top casing that attaches to the side casing opposite the structural support forming a cavity between the top casing and the front of the piezoelectric material that is surrounded by the side casing. The top casing is circular. The contact between side casing and top casing is circular. The top casing is less than approximately 50 microns, in thickness. The cavity is filled with a polymer. The polymer contains silicone. The polymer contains parylene. The polymer contains epoxy. The polymer contains polyimide. The polymer and top casing are preselected so as to be in acoustic resonance at a preselected frequency and to achieve a preselected impedance matching between the piezoelectric material and the tissue. Each of the electrically isolated regions (if present) is connected to each other in series. Each of the electrically isolated regions is connected to rectifiers. The rectifiers are diodes. The rectifiers are synchronous switches. The transducer is a send transducer, configured to convert electricity into acoustic waves. The transducer is a receive transducer, configured to convert acoustic waves into electricity. The transducer is electrically connected to the active implantable medical device. The medical device is a hearing aid. The medical device is a cochlear implant.

In general, in an aspect, a power conversion system is described having a send transducer as described above, operatively coupled to an electrical load, and a receive transducer as described above, such that when the load is activated the system presents a constant impedance to the receive transducer. Implementations may include one or more of the following features. The volume fraction of the receive transducer's pillars and the volume fraction of the receiver transducer's filler material are preselected so as to match the impedance of the electrical load that is attached to the send transducer. The surface area of the receive transducer's top casing is greater than that of the send transducer's top casing. The acoustic waves have a frequency greater than approximately 200 kHz. The send transducer is insertable into a conchal bowl of a subject's ear, and the receive transducer is implantable in the pinna of that ear. The send transducer is mountable on the back of the subject's ear and the receive transducer is implantable in the pinna of that ear.

In general, in an aspect, a method of manufacture of a curved piezoelectric composite is described, the method including making regular cuts in two directions upon the front of a piezoelectric material, forming pillars; pouring uncured epoxy into the cuts surrounding the pillars, forming a filler material; pushing a backing substrate against a curved mold so as to shape it; and attaching the backing substrate. Implementations may include one or more of the following features. The front of the piezoelectric material is lapped to a predetermined thickness. Electrode layers are deposited upon the pillars. As a final step, the epoxy may be cured or be allowed to cure.

In general, in an aspect, a power link for powering active implantable medical devices is described having a transducer that includes an acoustic matching layer containing polymer and a top casing containing titanium, in which thickness and composition of the matching layer and top casing as preselected so as to be in acoustic resonance at a preselected frequency and to achieve a preselected impedance matching between the piezoelectric material and the tissue. Implementations may include one or more of the following features. The matching layer is surrounded by a spacer that is approximately ring-shaped. There is an alignment magnet that surrounds the piezoelectric material. The transducer is a receive transducer and is implantable in the mastoid of a subject.

With the foregoing and other advantages and features of the invention that will become hereafter apparent, the nature of the invention may be more clearly understood by reference to the following detailed description of the invention and the appended claims.

DESCRIPTION

Parts Legend 101 substrate printed circuit board, substrate PCB, structural support
102 piezoelectric material
103 backing spacer
105 acousto-mechanical transducer
107 acoustic spacer
109 top casing
111 space
113 pins
115 side casing
117 outer casing
125 front of the piezoelectric material
127 back of the piezoelectric material
129 air pocket
131 via (filled)
133 electrical connection
141 electronics and power circuitry
201 send transducer, transmit transducer
203 receive transducer
210 active implantable medical device
212 wires to implantable device
214 wires to driver circuitry
216 acoustic waves
218 tissue
220 acoustic coupling medium
301 pinna
303 transmit unit, send transducer
305 magnet
307 clip 309 back of pinna
601 electrical load
603 filter capacitor
605 rectifier
607 piezoelectric region
609 piezoelectric region
611 piezoelectric region
613 piezo ground plane
701 common electrode
703 electrically isolated regions
705 piezoelectric (regions)
801 send transducer, transmit transducer
803 receive transducer
812 wires to implantable device
814 wires to driver circuitry
816 acoustic waves
818 tissue
820 acoustic coupling medium
901 pillars (of piezoelectric material)
903 filler material
1001 send transducer, transmit transducer
1301 pinna
1303 transmit unit, send transducer
1401 feed-through cover
1403 top casing
1405 matching layer spacer ring
1407 piezoelectric material
1409 alignment magnet
1411 flex substrate
1413 outer casing
1415 feed-through
1417 bottom casing By "spherical cap", it is meant that shape that resembles a portion of a hollow sphere cut off by a plane.

Certain aspects of transducers of the present invention are illustrated in FIGS. 1-4. An acousto-mechanical transducer 105 is assembled onto a structural support 101 made from, e.g., a printed circuit board (PCB), part of the housing, or any solid and flat supportive material appropriate to the application. In some embodiments, the PCB 101 is circular. In some embodiments, adhered to the support is a backing spacer 103, and adhered to the backing spacer 103 is a piezoelectric material 102. In some embodiments, the backing spacer 103 and piezoelectric material 102 are circular and the backing spacer 103 has an inner diameter equal to the piezoelectric material 102 less a small overlap. By contacting the piezoelectric material 102 at only its periphery, the backing spacer 103 when present maintains an air pocket or gap 129 behind the piezoelectric material 102 to provide a low-impedance condition that is desirable for good performance; additionally, the backing spacer 103 forms a seal between the piezoelectric material 102 and the structural support 101, preventing fluids such as encapsulating epoxy from filling the back 127 of the piezoelectric material 102. The space 129 defined by the backing spacer 103 between the remaining surrounding structure (ie the PCB 101) is planar and has a uniform thickness spanning across the back side of the piezoelectric material 102.

Also adhered to the structural support 101 is an acoustic standoff spacer 107, which is used to maintain the correct space 111 between the front 125 of the piezoelectric material 102 and the top casing 109. The size of the space 111 determines much of the acoustic performance of the transducer 105. The acoustic standoff spacer 107 features pins 113 that allow for the flow of polymer, e.g., encapsulating epoxy, to the front 125 of the piezoelectric material 102 during manufacture. This encapsulating epoxy acts as an acoustic matching layer for device performance and provides strength to the acoustically transparent casing top 109. The acoustic standoff space 107 is spaced radially outwardly from the periphery of the piezoelectric material by a uniform radial distance such that the resulting annular gap between the periphery of the piezoelectric material is uniform. The acoustic space 107 is further arranged to support the top casing 109 such that the spacing 111 between the front side of the piezoelectric material and the remaining surrounding structure (ie the top casing 109) is planar and has a uniform thickness spanning across the front side of the material 102.

Figure 13:
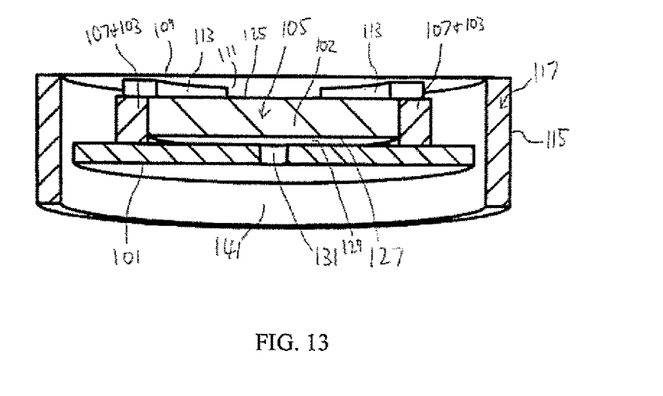
FIG. 13 shows a section view of an acousto-mechanical transducer.

In some embodiments, the acoustic spacer 107 and pins 113 are combined with the backing spacer 103. As such the combined backing and acoustic spacer contains the structure and functionality from items 103, 107, 113. Such a combined backing and acoustic spacer can be mounted on the structural support 101 and contacts the perimeter of the piezoelectric material 102, thus forming the air pocket 129 between 101 and 102. The combined backing and acoustic spacer also contacts the top casing 109 to form the correct space 111 for acoustic performance of the device. See FIG. 13.

The side 115 of the outer casing 117 is around the parameter of the transducer and in some embodiments is circular. Generally, the side 115 is thick with respect to the thickness of the top 109. This arrangement is to provide structural robustness along the side, while the top plate remains optimal for acoustic performance. On its own, the top 109 might not have been sufficiently strong to withstand the rigours of use; however, the polymer adds rigidity.

The piezoelectric material 102 is adhered to the backing spacer 103, which is then adhered to the structural support 101. Using a via (pass-through) 131 in the PCB 101 behind the piezoelectric material 102, an electrical connection 133 to the back 127 is made and the via 131 is then sealed, providing a permanent air gap 129 behind the piezoelectric material 102. A chamber containing additional electronics and power circuitry 141 may be placed under the PCB 101 (opposite the air gap 129), allowing space for electrical connection to the transducer and to power components. The acoustic standoff spacer 107 is then adhered to the structural support 101. The top casing 109 is attached (e.g., by welding) to the side casing 115 to form the outer casing 117. In some embodiments, the casing is attached to the rest of the transducer assembly by inverting the case, inserting the assembly into the case with the standoff spacer 107 pressed against the top casing 109. The casing is then filled with encapsulating epoxy, providing the acoustic matching layer required for performance and the required strength for the completed acousto-mechanical transducer.

Figure 1:
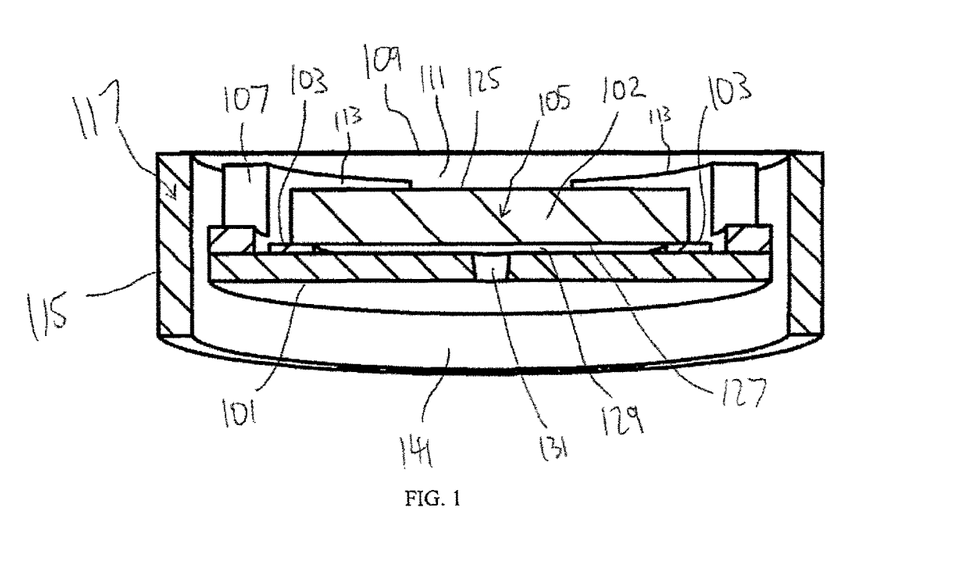
FIG. 1 shows a section view of an acousto-mechanical transducer.
Figure 2:
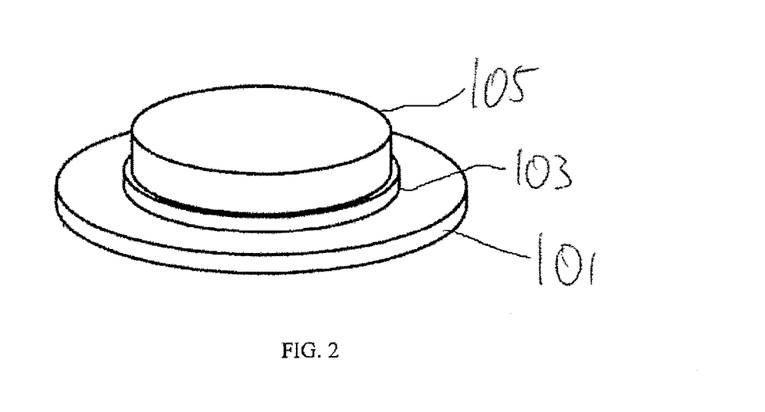
FIG. 2 shows a perspective view of part of an acousto-mechanical transducer.
Figure 3:
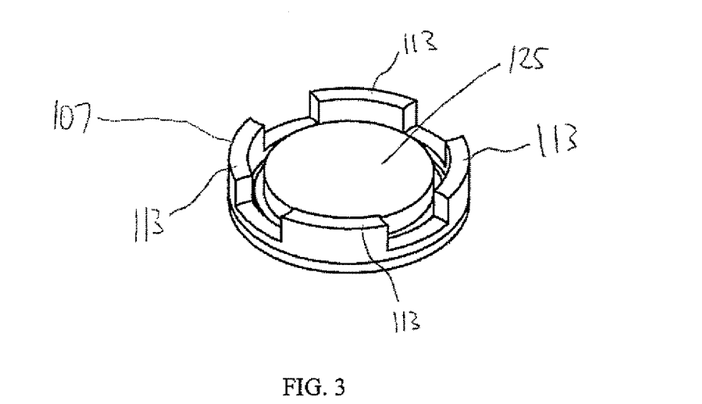
FIG. 3 shows a perspective view of part of an acousto-mechanical transducer, further assembled.
Figure 4:
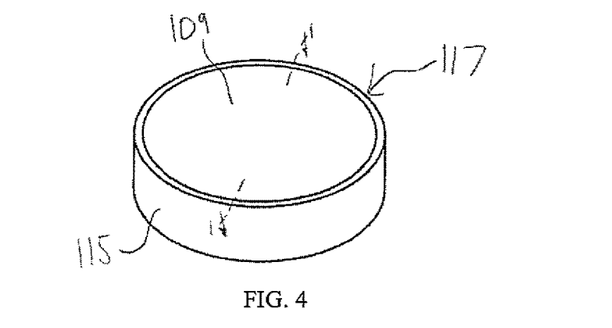
FIG. 4 shows a perspective view of part of an acousto-mechanical transducer, further assembled (polymer not shown).
Figure 5:
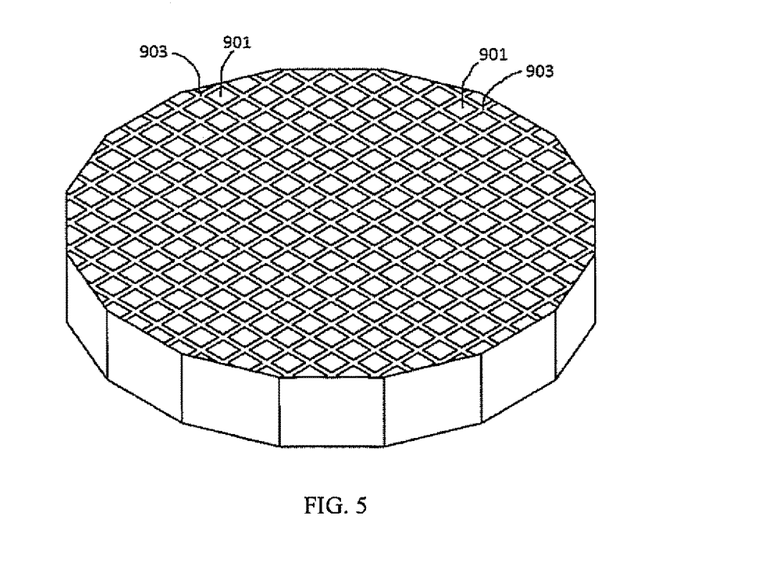
FIG. 5 shows a detail view of the piezoelectric material pillars surrounded by filler material.

Separation of the piezoelectric material into pillars 901 as in certain embodiments of the present invention can make the material flexible and capable of being curved and therefore focused (see FIG. 5). Focusing can be achieved after filling the kerfs with filler material 903, e.g., epoxy, but before the epoxy cures by curving the composite transducer around a mold of the desired shape. For spherical curving that mold may be a ball bearing. Even after setting, certain epoxies are known to become soft and malleable when they are heated, so an alternative method of curving a composite transducer made from such an epoxy is to heat it after the epoxy has cured, curve it around a mold and allow it to cool down to retain its new shape. The body of piezoelectric material includes a continuous and uninterrupted portion spanning across the backside from which the pillars protrude. The continuous portion of the body has a uniform thickness from the backside across the full width and length of the body which is sufficiently thin to allow some flexing into a non-planar shape if desired. The pillars 901 protrude from the continuous portion of material at the backside of the body to the front side of the body of piezoelectric material 102 such that the pillars extend in a direction which is perpendicular to the front and back sides of the body. Furthermore the front ends of all of the pillars 901 terminate at a substantially common surface collectively defining the front side of the body of piezoelectric material. The common surface at the front side may be planar, convex, concave, or form part of the surface of a cylinder for example. The pillars 901 are arranged in a uniform grid pattern or array so as to be evenly spaced apart from one another in lateral (widthwise) and longitudinal (lengthwise) directions which are perpendicular to one another along the common surface. The pillars 901 are fully isolated from one another from the front side to the continuous portion of the piezoelectric material which fully spans the back side of the body of piezoelectric material.

In order to achieve unidirectional transmission of acoustic energy from one face of a transducer the other face should generally make contact with a material of very different acoustic impedance from the transducer material. The most common option is to provide "air-backing" since the acoustic impedance of air (403 Rayl at body temperature) is very different from that of most lead-based piezoelectric materials (20-30 MRayl). Typical reflection coefficients at an air-backed face exceed 99.99%. However, in order to maintain the mechanical strength of an implanted receiver unit, particularly one with a thin shell, a continuous air pocket throughout the volume of the casing is undesirable as it makes it easy for the casing to buckle under external loading. From a manufacturing and mechanical robustness viewpoint, a support or series of supports for the transducer would be preferred, but when such supports contact the transducer they provide an acoustical pathway for energy to leave the transducer through the back face and this will act as a source of loss. To avoid this problem, in some embodiments, supports are used that minimize contact area with the back face of the piezoelectric material. In some embodiments, support is provided by a plurality of pins that make contact with the transducer only at very small points. These pins act to prevent bending and ensure mechanical robustness while minimizing the area over which acoustic energy can be lost. In another embodiment the transducer is supported by a rigid, toroidal ring that, owing to its toroidal shape, supports the piezoelectric only along a narrow circle of contact but, again, provides support against bending of the case.

In some embodiments, a power conversion system includes two transducers, one configured as a send unit and the other as a receive unit. In some embodiments, the acoustic waves used to transmit power through between the two units is between approximately 200 kHz and approximately 5 MHz. In some embodiments, the power requirements are between approximately 10 mW and approximately 100 mW. In some embodiments, the power requirements are between approximately 10 mW and approximately 500 mW. In some embodiments, the power requirements are greater than approximately 500 mW.

In order to achieve a high efficiency, an ultrasonic power link or power conversion system is ideally designed to minimize acoustic and electrical losses. Acoustic losses in tissue occur due to scattering and absorption of sound by cells and are described by an attenuation coefficient $\alpha$ in dB/cm. Typical values for skin, fatty tissue and muscle are 0.35, 0.40 and 0.74 dB/cm respectively at 1 MHz. Attenuation tends to increase with increasing frequency according to a power law whose exponent depends on the tissue type (i.e., 0.6 for skin). If acoustic energy at 1 MHz generated by the transmitter is perfectly absorbed by a receiver 5 mm away, then the loss of power due to the tissue is only on the order of 4-10% for tissues consisting of fat, muscle and skin. However, in many systems, receiver transducers are not 100% absorbing of incident acoustic power and tend to reflect some fraction of it. This reflected acoustic energy returns to the transmitter where it is either absorbed or reflected again. Doubly reflected acoustic energy has another chance of being reabsorbed at the receiver, but must travel through three times as much tissue as acoustic energy that was directly absorbed. Maximizing the efficiency of an ultrasonic power link may often involve, then, designing to absorb as much acoustic energy as possible on the first pass through tissue and minimize the reflection of energy from the receiver.

Reducing the reflected power has some additional benefits since the superposition of incident and reflected acoustic waves in the tissues tends to form standing waves with a higher peak intensity than the emitted wave. The regions of high peak intensity absorb more acoustic energy and so heat up and are also at greater risk of cavitation. As a result, the maximum power that can be delivered safely through an ultrasound power link will be higher if reflections at the receiver can be minimized.

Reflections at the receiver can be minimized in a number of ways. An acoustic matching layer may be applied to the surface of a transducer to create destructive interference of waves reflected off the boundaries of multiple surfaces. For example, a matching layer that is ¼ of a wavelength in thickness and that consists of a layer of material with an acoustic impedance that is the geometric mean of the acoustic impedance of the piezoelectric material and tissue will create no reflection at a particular wavelength.

Reflections can also occur if acoustic energy enters the piezoelectric material and is not converted into electrical energy before exiting the material. This sort of reflection may be reduced by using a piezoelectric material with a high electromechanical coupling efficiency, usually denoted as k with a subscript that depends on the particular geometry of the transducer. A material in which acoustic energy was perfectly converted into electrical energy would have a value of k of 1. For a plate transducer that is much wider than it is thick, the relevant electromechanical coupling is $k_t$. For many relaxor-PT materials, $k_t$ can exceed 0.6 as compared with 0.5 in more traditional piezoelectrics like PZT ceramics.

The electromechanical coupling efficiency, k, can be further increased and so the reflection of the receive transducer further decreased by cutting a piezoelectric plate into a series of pillars where each of the pillars has a smaller width dimension than thickness dimension. The gaps between the pillars can then be filled with a material with a lower stiffness than that piezoelectric. In some embodiments this low stiffness material is an epoxy. In other embodiments it may be another polymer. In yet other embodiments it may be air. The presence of the gaps filled with low-stiffness material allows the piezoelectric material to contract laterally while expanding transversely which in turn allows it to create a larger amount of motion for the same amount of applied electrical energy. This greater motion translates into a greater electromechanical conversion efficiency hence a higher k. By selecting an appropriate volume fraction of piezoelectric material and soft filler material, the electromechanical conversion efficiency may be enhanced nearly up to a maximum value of $k_{33}$ which for PZT is approximately 0.7 and for relaxor-PT materials can exceed 0.9.

The technique of cutting pillars of a piezoelectric material to increase electromechanical coupling has been previously used in ultrasonic imaging systems, but has heretofore not been used in a power conversion system with increased absorption of acoustic power at the receiving transducer.

In some embodiments, the power conversion system can be made more efficient by dicing the piezoelectric material into a set of pillars, the gaps between which are filled with a softer material (epoxy, in one preferred embodiment) that allow the piezoelectric material the freedom to expand laterally when under load. In some embodiments, piezoelectrics were fabricated using a dice and fill technique. First, solid samples of PMN-PT were adhered to a substrate and were cut into pillars using a micro-dicing saw. Encapsulating epoxy was then poured between the pillars and allowed to cure. Once cured, the filled composites were lapped to the designed thickness and chromium and gold electrode layers were deposited using a thermal evaporation process. In one embodiment, the pillars were 440 um wide and the cuts between them 100 um wide. Selection of the cut sizes can be made with respect to their respective volume fractions for better performance; see below.

In some embodiments, the sensitivity of acoustic power links to lateral and angular alignment is decreased. The sensitivity to alignment can be reduced by a combination of focusing of acoustic energy, creating a mismatch in the size of the receive and transmit transducers and electrically isolating different regions of the receive transducer from each other. Another kind of reflection may occur in an ultrasonic power link, particularly in one where the receive transducer is non-uniformly insonified. Non-uniform insonification will occur, for instance, if the shape or size of the receive and transmit units are different or if the transmit unit is focused so that the size of the focused beam on the receive transducer is smaller than the transducer. In such circumstances, non-uniform insonification will create a non-uniform surface charge through the piezoelectric effect. Since there is a single electrode covering the surface of the piezoelectric, this charge will flow across the surface of the transducer to make the voltage equal everywhere. In the regions of low insonification this charge will create mechanical stress due to the reverse piezoelectric effect that will generate strain and cause acoustic energy to be re-radiated out from the transducer. This re-radiated acoustic energy is not converted into electrical energy and so represents a source of loss that reduces the link efficiency.

Figure 9:
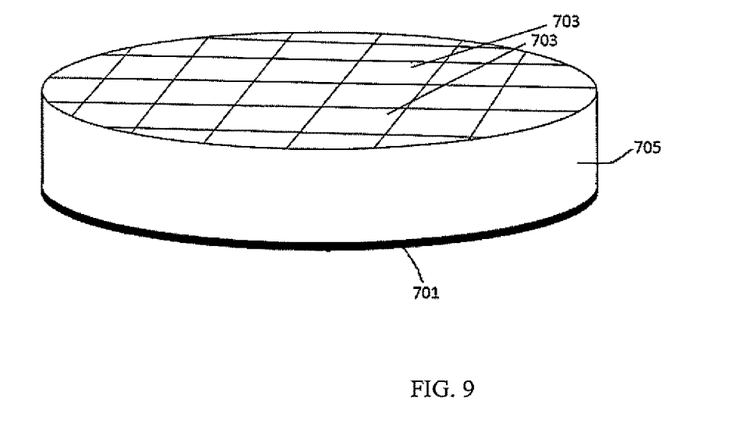
FIG. 9 shows a perspective view of discrete electrically isolated regions in a transducer.

In some embodiments, the system may be designed so as to achieve as uniform an insonification as possible at the receive transducer by, for example, defocusing the transmitted acoustic energy. In other embodiments (see FIG. 9), a surface electrode of the receive transducer may be divided into smaller, electrically isolated regions 703, approximately the same size as the focused ultrasound beam on the receive transducer. The paired electrode for each region is a common electrode 701. Each piezoelectric region 705 so defined will be uniformly insonified since the beam will either land on the region or not. Electronics in the receive unit may then be used to extract electrical energy from each of the isolated regions.

Electrical isolation of the different regions prevents lateral charge flow across the transducer surface and so prevents re-radiation of acoustic waves. With different regions electrically isolated, the receiver can be made larger than the transmitter, which can be useful in reducing the sensitivity of the system to lateral misalignment (see below).

Figure 6:
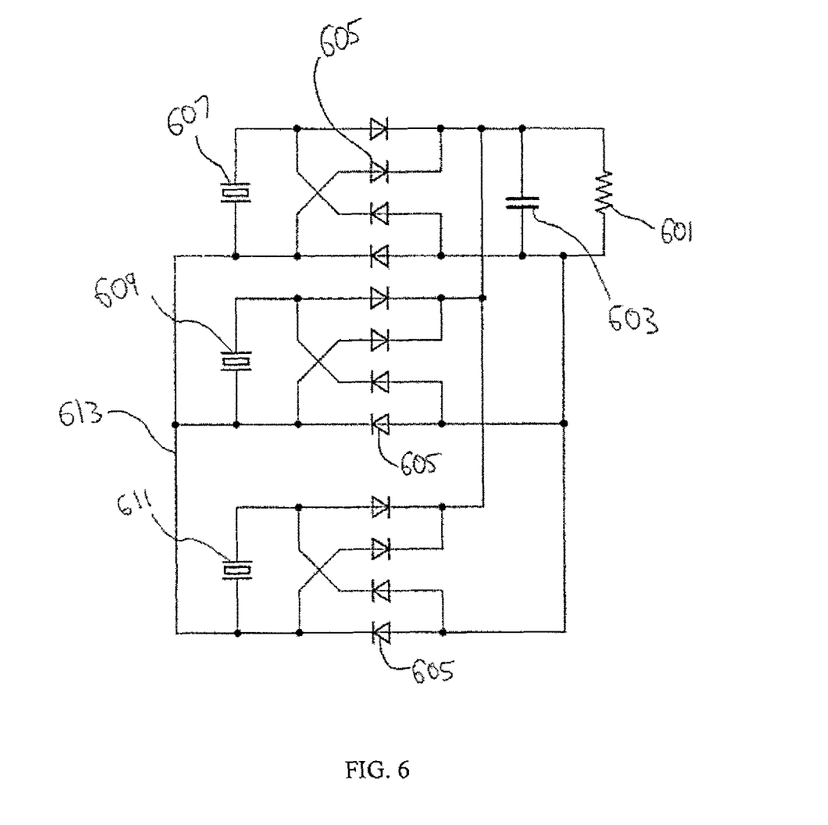
FIG. 6 shows a circuit diagram that connects electrically isolated regions of piezoelectric material.

In some embodiments (see FIG. 6) electronics have a rectifier 605 attached to each electrically isolated regions 607, 609, 611 and to a ground plan 613 so that charge can only flow from each region to the load 601 but not from one region to another. In some embodiments, a filter capacitor 603 is interposed between the load 601 and the rectifiers 605. In one embodiment the rectifier consists of a diode-based rectifier, and a Schottky-diode based rectifier in preferred embodiments. In other embodiments rectification may be achieved with a field—effect transistor, bipolar junction transistor or other switching element that switched synchronously with the frequency of the incident acoustic radiation so as to only allow charge to flow in one direction through the load. In yet another embodiment, switches such as transistors are used to connect the electrically isolated regions in series in order to increase the voltage seen by the load. In some embodiments voltage detection circuitry is used to control switching within the rectifier circuit. In one possible embodiment, a voltage detection circuit is used to determine which regions are most highly insonified (as these regions will have the largest voltage) and to connect those regions to the load. In another embodiment voltage detection circuitry is used to compare the load voltage to the voltage of different insonified regions and to connect regions to the load in the order of their voltage levels. For example, the region with the highest voltage would be connected to the load until its voltage dropped to the level of the region with the second-highest voltage which would then also be connected to the load and so on. In yet another embodiment, region with lower levels of insonification may be connected to a switched inductor boost-mode converter in order to increase the voltage level generated by the region to the voltage of the most highly insonified region. In some embodiments voltage detection circuitry is used to control switching in the boost-mode converter. In yet other embodiments this voltage boost is achieved by a magnetic transformer. In yet other embodiments it is achieved by a piezoelectric transformer.

One of the key difficulties in the art of power link design, be they ultrasonic or inductive, is the need to accurately align the transmit and receive transducers in terms of both lateral translation and angle in order to achieve high efficiency power transmission. In an ultrasonic link a lateral misalignment of a significant fraction of the transducer diameter will result in a significant fraction of the transmitted energy missing the receiver and hence not being converted into electrical energy. This may be somewhat alleviated by using large diameter transducers, but this is inconvenient from the point of view of packaging, form factor and implantation.

An angular misalignment also leads to reduced efficiency. If the receiver and transmitter have the same diameter and are unfocused and the angle of the beam emitted by the transmitter differs from the direction of the surface normal by an angle φ, then the phase of the beam at opposite edges of the transducer will be different by an amount given as $$\sin\phi = \frac{\lambda}{2w}$$

Where λ is the wavelength and w is the size of the insonified region on the receive transducer, which is roughly equal to the transmitter transducer diameter if the beam is unfocused. If the phase of the acoustic wave differs over the surface, then this will lead to a non-uniform insonification since at any given moment the pressure seen at different edges of the transducer is different. If the angle is large enough it is possible that some fraction of the surface will see negative pressure while the remainder sees positive pressure. This will lead to little net surface displacement and to most of the input acoustic energy being reflected rather than absorbed.

Alignment sensitivity can be reduced by focusing the transmitted ultrasound beam so that only a small region of the receive transducer is insonified. If this is done, then the w in equation 1 is reduced and so a larger angle mismatch is required to create significant differences in the phase of the pressure over the receive transducer surface.

Focusing also helps with lateral translation insensitivity if the receive transducer is significantly larger than the transmit transducer because the transmit transducer can be translated by almost the full diameter of the receive transducer while keeping all of the transmitted acoustic power incident on the receiver. Consequently, in some embodiments there is a small, focused transmitter and a large receiver using the techniques of the previous section to define electrically isolated regions in which the charge generated by the incident acoustic pressure is concentrated. Such a power link will exhibit a high degree of alignment insensitivity while maintaining high efficiency.

In some embodiments, the impedance of the receive transducer is adjusted by changing the relative volume fraction of piezoelectric and soft material. In order to maximize the amount of power delivered to an electrical load, the impedance of the source of power must be matched to that of the load. For real valued loads the maximum power transfer is achieved when the source and load impedances are exactly matched. While impedance matching can be achieved with an electrical transformer, such devices are large and bulky and often not suitable for use in an implanted device. In some embodiments, different volume fractions are used for the piezoelectric composite in the transmit and the receive transducers. The source electrical impedance of the receive transducer is then determined in part by the volume fraction of piezoelectric versus filler material.

The effective electrical source resistance seen by an acoustic transducer $$R_{ao} = \frac{2(k^t)^2}{\pi^2 f_0 C_0}$$

operating at its resonance frequency and perfectly acoustically coupled to water is given as Where $R_{ao}$ is the radiation resistance, $k^t$ is the electromechanical coupling, $f_0$ is the center frequency and $C_0$ is the clamped capacitance. The clamped capacitance is determined by the volume fraction. If x is the fraction of piezoelectric material and (1−x) the fraction of filler, the capacitance is $$C_0 = \frac{A\varepsilon_0(x\varepsilon_s^P + (1-x)\varepsilon_f)}{t} \approx \frac{A\varepsilon_0 x\varepsilon_s^P}{t}$$

Where $\varepsilon_s^P$ is the clamped dielectric permittivity of the piezoelectric material, $\varepsilon^f$ is the permittivitty of the filler, A is the area of the transducer and t is its thickness. The approximation holds because the permittivity of most piezoelectrics is much higher than that of most filler materials.

Because of these two equations, one can achieve a different radiation resistance by selecting an appropriate value of the volume fraction x. In a particular application one would select an appropriate x to achieve an $R_{ao}$ to match the resistance of the load being driven.

In some embodiments, the transducer casing and spacing between case and piezoelectric is selected so as to be both hermetic and acoustically transparent. An example of a hermetic material is titanium. A titanium housing (side and top casings) with a thin top casing (approximately less than 50 microns) can form an acoustic window that minimizes acoustic losses into the housing while remaining a support structure. Implanted medical devices need to be packaged in a material that is biocompatible and highly durable so that it can survive in the body for many years without developing leaks or cracks. Many implants designed for long-term use are manufactured from titanium, a metal that is known to exhibit excellent bio compatibility, strength and durability. Ideally, the implanted portion of an acoustic power link would also be made of titanium. Titanium, however, has an acoustic impedance of 14.06 MRayl as compared to approximately 1.5 MRayl for tissue. The acoustic power reflection at the boundary between two bulk materials with different acoustic $$R = \left(\frac{Z_1 - Z_2}{Z_1 + Z_2}\right)^2$$

impedances is governed by the equation:

where $Z_1$ and $Z_2$ are the impedances of the two materials. For titanium and tissue the reflection is 65%, making it very difficult to transmit acoustic energy through titanium of typical thickness. However, if the titanium layer is made very thin compared to the wavelength, then the reflection coefficient can be reduced. The reflection coefficient can also be reduced by using interference of the reflections from the transducer-titanium and the titanium tissue interfaces to destructive interfere in the reflected direction.

It is generally not practical to keep the entire housing of a titanium case 25 um thick. Such a thin housing will have poor mechanical strength and cannot be manufactured using standard hermetic manufacturing processes such as laser welding which generally requires 150 um or thicker titanium at the weld site. To overcome this problem, the case can be manufactured from thick titanium and then the titanium can be thinned in the region directly over the transducer. In some embodiments thinning is performed by stamping the case prior to final assembly. In other embodiments it is performed by precision milling. In other embodiments it is performed by chemical etching. In yet other embodiments it is performed by laser ablation.

In some embodiments of the present invention we construct a mass spring system comprising a "spring" polymer layer of thickness $t_p$ and Young's modulus E in contact with the transducer. In one embodiment this polymer layer is comprised of epoxy. In another embodiment it is comprised of parylene. The polymer layer is attached to a "mass" layer consisting of the titanium casing of the housing. The thickness $t_m$ of the housing is selected to give the correct mass for the mass-spring system needed to have the desired resonant frequency and impedance matching. If the transducer has a resonance frequency of omega$_0$ and a characteristic impedance $Z_p$, then the thickness of the polymer layer and the thickness of the titanium housing are selected to satisfy the following equations:

$$t_m = \sqrt{\frac{Z_R Z_P \rho^2}{\omega_0^2}} \quad t_p = \sqrt{\frac{E}{\omega_0^2 Z_R Z_P}}$$

Where $Z_R$ is the radiation resistance of water and $\rho$ is the density of titanium.

In one embodiment for a PMN-PT composite transducer with an acoustic impedance of 12 MRayl and a center frequency of 1 MHz, the spring layer includes a 197 μm thick layer of parylene-C and a titanium housing that is 127 μm thick. When the transducer is water loaded, looking into such a spring layer, the transducer sees an acoustic impedance on resonance of 12.7 MRayl, a very good match for its characteristic impedance. In general, such layers will be between 50 and 300 μm thick which makes them convenient for manufacture through vapor deposition and/or sputtering techniques.

Figure 8:
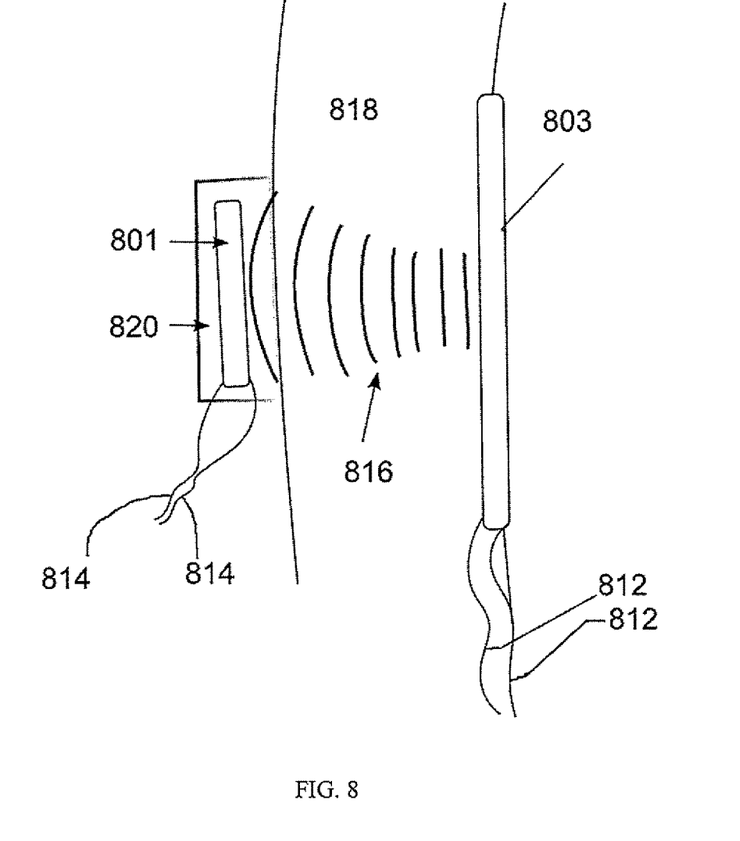
FIG. 8 shows an embodiment of a power conversion system.

Transducers of the present invention can be used to power many different implanted devices. In some embodiments, the device is a cochlear implant. In some embodiments, the device is an implanted hearing aid. In some embodiments, the device is an artificial pacemaker. The power requirements of such devices vary; in some embodiments, devices generally draw relatively low levels of power, in the few to tens of mW range. See FIG. 8 for the general construction of a power link in such an application, in which a send transducer 801 surrounded by appropriate acoustic coupling medium 820 is electrically connected to driver circuitry (not shown) by wires 814. The send tranducer 801 produces acoustic waves 816 that are transmitted through tissue 818 to the receive transducer 803, which in turn converts the acoustic energy into electricity that is transmitted to one or more implantable devices (not shown) by wires 812.

Cochlear implants consist of two parts, an electrode that is inserted into the cochlea and a unit consisting of the power link and internal demodulation and signal processing electronics. For inductive links the power link unit is implanted in a recess in the posterior part of the skull on the same side as the implant. The unit contains an implanted permanent magnet, and the external unit with its own magnet attached to the skull on the outside where it is held in place by the magnet. Such units typically contain a 25-50 mm diameter induction coil, and so must be at least 25-50 mm in size.

Figure 7:
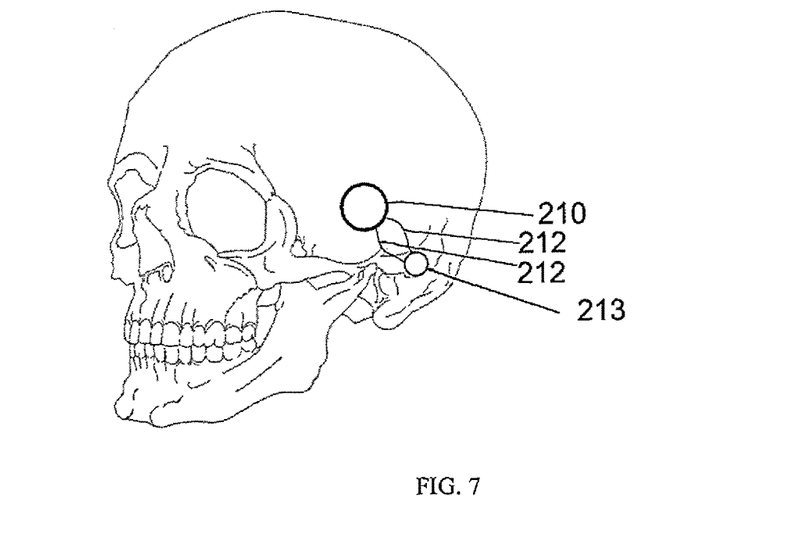
FIG. 7 shows a receive transducer attached to an active implantable medical device.

With an acoustic power link, both the implanted and the external parts of the link may be made much smaller. For example, in some embodiments the transmitter has a 5 mm diameter and the receiver an 8 mm diameter. These dimensions are small enough to implant in the temporal bone just posterior to the ear canal. FIG. 7 shows a possible implantation site, with the receive unit 203 electrically connected to an implantable device 210 by wires 212. With the link having been made insensitive to alignment through the techniques disclosed above, it is possible to align the transmit and receive units without requiring an implanted magnet by relying on anatomical features.

Figure 10:
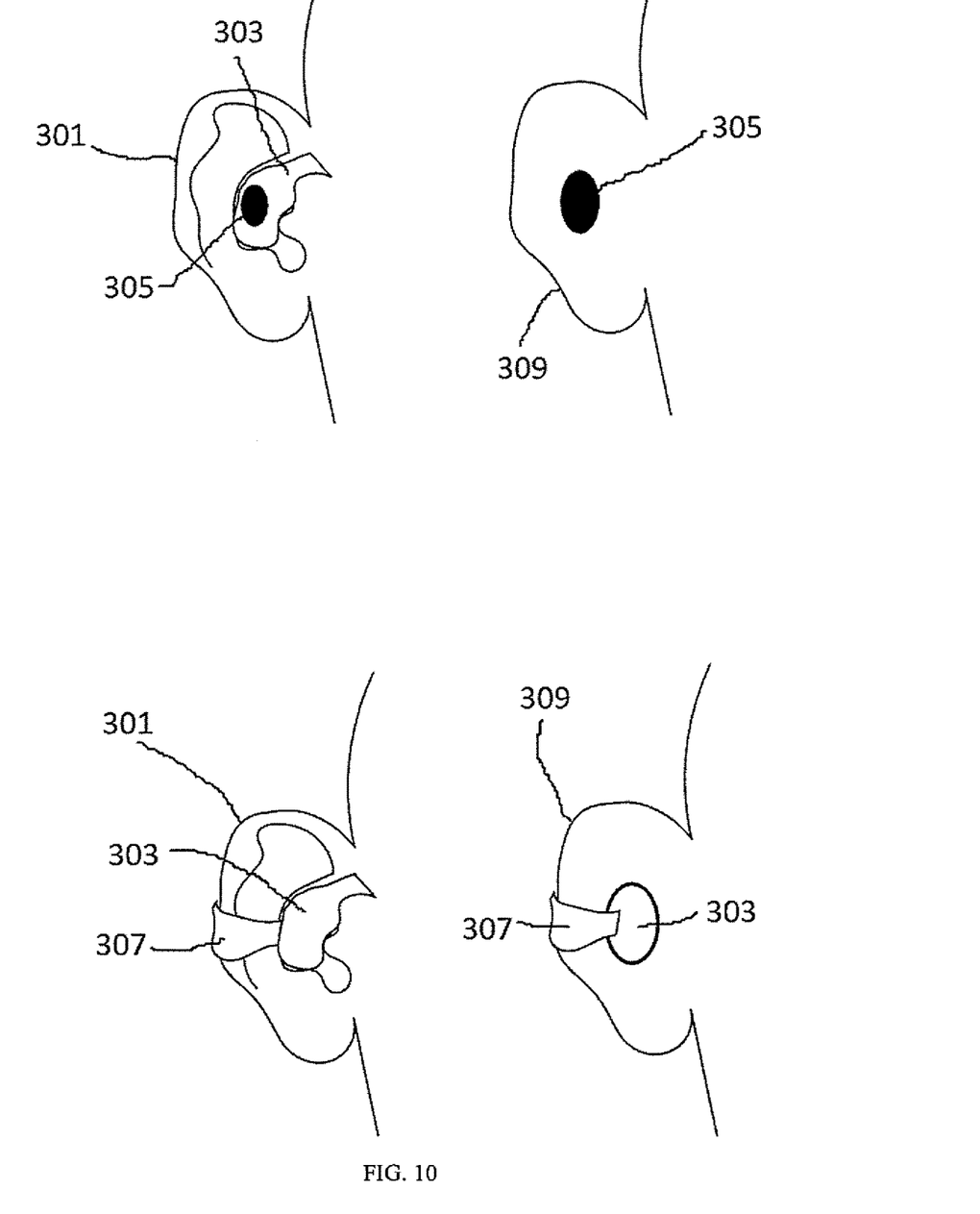
FIGS. 10 through 12 show various embodiments of power links attached to active implantable medical devices.
Figure 11:
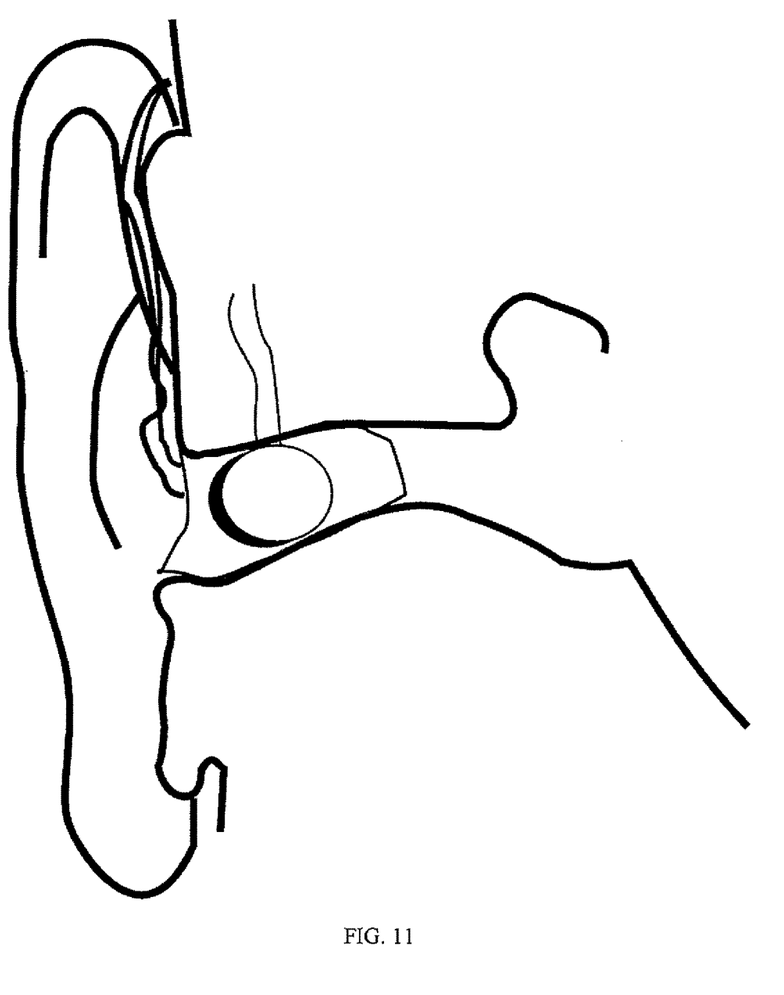
Figure 12:
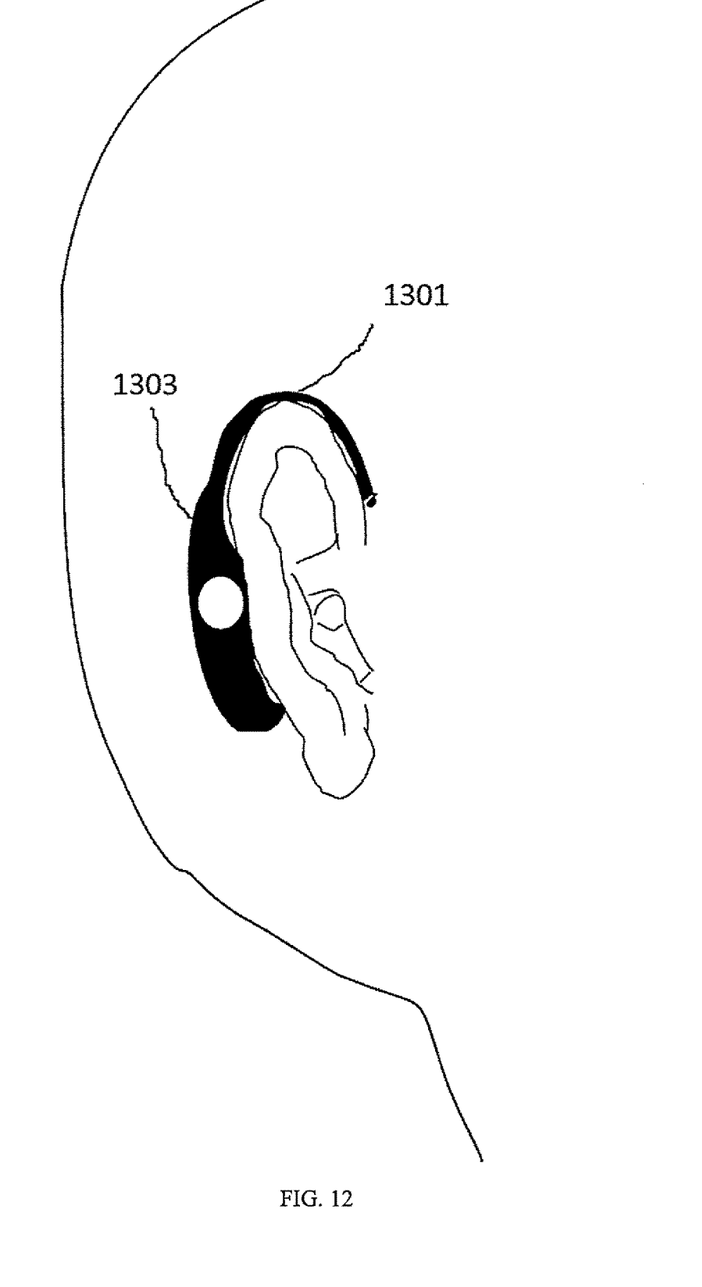

See FIGS. 10-12 for other possible implantation sites.

In one embodiment the transmitter is housed in a "behind the ear" ear unit that hangs off the pinna by a hook and the receiver is implanted on the mastoid bone directly posterior to the ear. The two devices are aligned by virtue of the anatomical shape of the pinna and mastoid.

In another embodiment the transmitter is housed in a unit that sits in the conchal bowl of the pinna. The unit may be held in place by a knob that sits in the fossa triangularis. The shape of the unit may be individually molded to each patient. The receive unit is surgically implanted in the pinna using a posterior approach and a wire running along the pinna is used to connect to the electronics of the cochlear implant.

In yet another embodiment the transmitter is housed in a unit that fits into the ear canal and is pressed up against that posterior wall of the ear canal by pressure generated on insertion. The implanted unit is implanted in the posterior wall of the ear canal. In this embodiment the system may be designed to provide feedback to the user when a good alignment is achieved. This feedback may be acoustic, delivered through the cochlear implant or tactile delivered as, for example, a vibration of the transmit unit when good alignment is achieved.

Any of these three embodiments are also appropriate for powering implanted hearing aids other than cochlear implants. Other embodiments are also possible, e.g., for the powering of artificial pacemakers or other active implantable medical devices.

In some embodiments, an alignment magnet is present in each transducer assembly of the power link in order to enhance the placement of the send transducer with respect to the receive transducer. Selection of the size of each magnet depends on the size of each assembly, the required attractive force to maintain alignment when installed, the amount of tissue between the two magnets when installed, and the extent to which quality of computed tomography or magnetic resonance images will be impacted by the presence of a magnet. In preferred embodiments, the alignment magnet is placed around the piezoelectric material, avoiding interference with the acoustic pathway that would result from placement in front of the material. In some embodiments, the alignment magnet is of such thickness and depth as to serve as inner housing, supporting the piezoelectric material and maintaining air backing.

Figure 14:
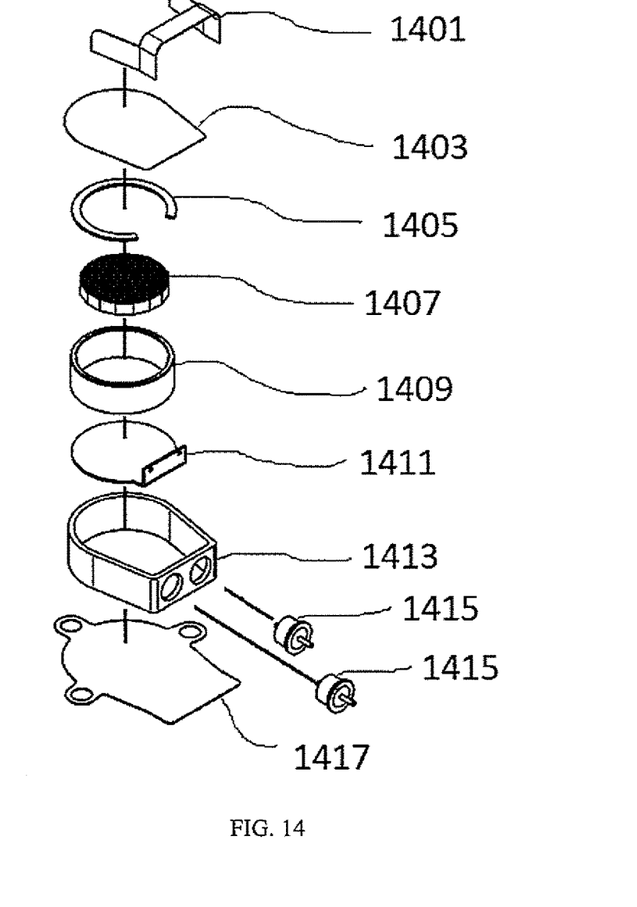
FIG. 14 shows an exploded view of an acousto-mechanical transducer.
Figure 15A:
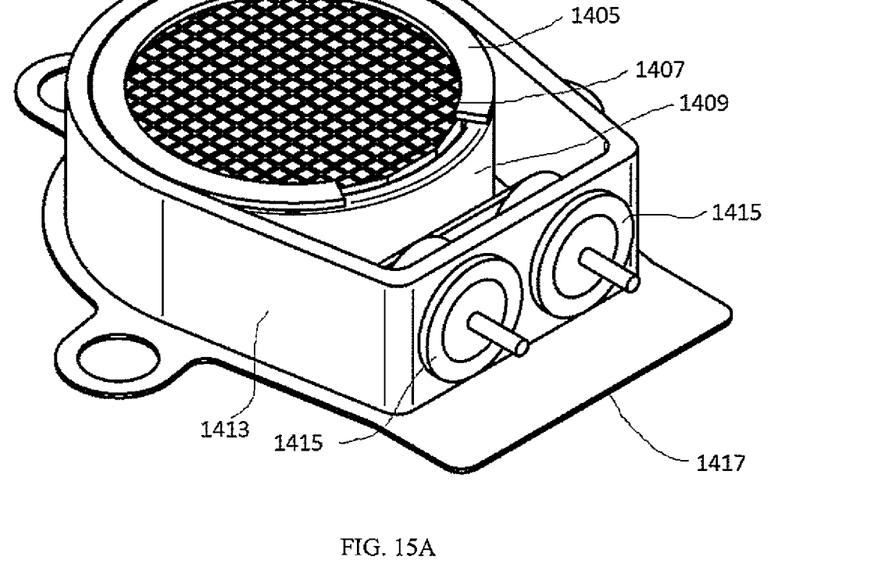
FIG. 15 shows a perspective view of an acousto-mechanical transducer, with and without top casing.
Figure 15B:
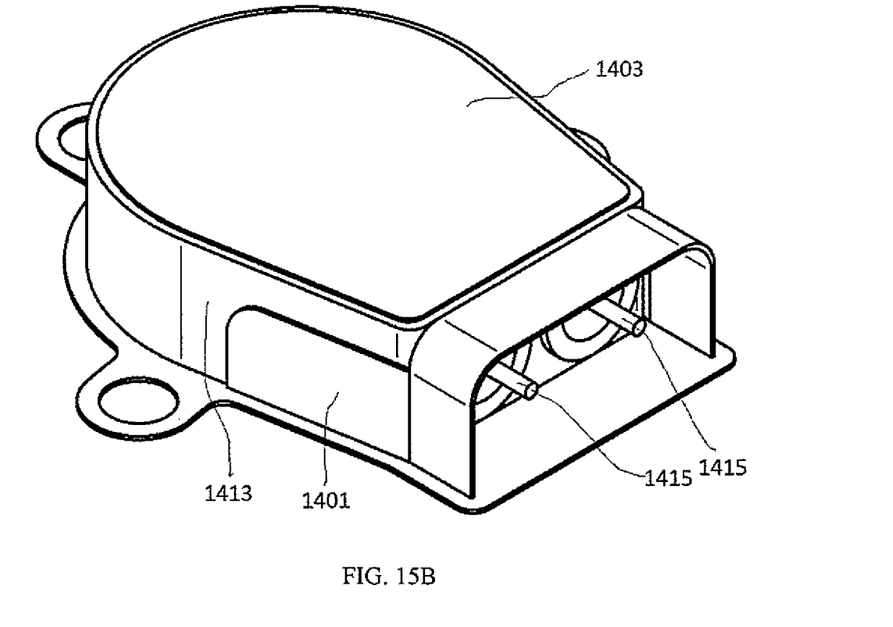

One embodiment of a power link is shown in FIGS. 14 and 15, in which each transducer assembly incorporates an alignment magnet. A piezoelectric material 1407 is topped with a spacer ring 1405 that is acoustically matched with the material and with the top casing 1403 that sits atop the ring 1405. The spacer ring 1405 is so constructed as to allow for the flow of polymer (not shown), e.g., encapsulating epoxy, to the front of the piezoelectric material 1407 during manufacture. This encapsulating epoxy acts as an acoustic matching layer, is surrounded by the spacer ring 1405 once assembled, is of a depth approximately equal to the distance between the front 1407 and the top edge of the spacer ring 1405 such that it is flush with the ring, and provides strength to the acoustically transparent top casing 1403. The material 1407 is surrounded by an alignment magnet which is in turn surrounded by an outer casing 1413. A flexible substrate 1411, having holes for electrical connections in and out of the transducer assembly, closes the cavity underneath the material 1407 while allowing for the connections to contact the material. A bottom casing 1417 attaches to the outer casing 1413 at its periphery. There are holes in the outer casing 1413 large enough to accommodate feed-through of the electrical connections. The 1401 feed-through cover is fashioned so as to attach to the top and outer casings. A hermetic seal is obtained for the transducer by welding.

The invention claimed is:

1. An acousto-mechanical transducer for the conversion of electricity into acoustic waves or vice versa, the transducer being attached to an active implantable medical device, the transducer comprising a body of piezoelectric material having a front and a back; and the transducer further comprising a backing spacer that contacts the body of piezoelectric material only at its periphery so as to maintain a space spanning the back of the body of piezoelectric material, in which: (i) the back of the body of piezoelectric material has a continuous portion, (ii) the front of the body of piezoelectric material has pillars of piezoelectric material that protrude from the continuous portion of the body of piezoelectric material and that are surrounded by a filler material, and (iii) the pillars are electroded such that each of the pillars is in an electrically isolated region.

2. The transducer of claim 1 in which the body of piezoelectric material comprises single-crystal relaxor-PT ferroelectric material.

3. The transducer of claim 1 in which the body of piezoelectric material comprises PMN-PT.

4. The transducer of claim 1 in which the body of piezoelectric material is curved.

5. The transducer of claim 1 in which the body of piezoelectric material is shaped as a spherical cap.

6. The transducer of claim 1 in which the medical device is a hearing aid.

7. The transducer of claim 1 in which the medical device is a cochlear implant.

* * * * *